United States Patent [19]

Spitzer et al.

[11] 4,174,386

[45] Nov. 13, 1979

[54] AEROSOL ANTIPERSPIRANT COMPOSITIONS WITH GOOD ADHERENCE TO THE SKIN

[76] Inventors: Joseph G. Spitzer, 44 Coconut Row, Palm Beach, Fla. 33480; Lloyd I. Osipow, 2 Fifth Ave., New York, N.Y. 10011; Marvin Small, 1100 Park Ave., New York, N.Y. 10028; Dorothea C. Marra, 107 Fernwood Rd., Summitt, N.J. 07901

[21] Appl. No.: 970,013

[22] Filed: Dec. 18, 1978

Related U.S. Application Data

[63] Continuation-in-part of Ser. No. 724,425, Sep. 17, 1976, abandoned, which is a continuation-in-part of Ser. No. 706,857, Jul. 19, 1976, abandoned, which is a continuation-in-part of Ser. No. 554,388, Mar. 3, 1975, Pat. No. 3,970,219, Ser. No. 670,913, Mar. 26, 1976, Pat. No. 4,019,657, Ser. No. 566,562, Apr. 9, 1975, abandoned, Ser. No. 620,448, Oct. 7, 1975, abandoned, and Ser. No. 628,283, Nov. 3, 1975, abandoned.

[51] Int. Cl.² ............................ A61K 7/32; A61K 7/34; A61K 7/38
[52] U.S. Cl. ............................ 424/47; 424/45; 424/46; 424/65; 424/66; 424/67; 424/68
[58] Field of Search .................. 424/45, 46, 47, 65, 424/66, 67, 68

[56] References Cited

U.S. PATENT DOCUMENTS

| | | | |
|---|---|---|---|
| 3,725,540 | 4/1973 | Wahl | 424/65 X |
| 3,903,258 | 9/1975 | Siegal | 424/47 X |
| 3,929,986 | 12/1975 | Bouillon | 424/68 X |
| 3,953,450 | 4/1976 | Bouillon | 424/68 X |
| 3,956,352 | 5/1976 | Bouillon | 424/68 X |
| 3,963,833 | 6/1976 | DeSalva | 424/68 |
| 3,968,203 | 7/1976 | Spitzer | 424/47 |
| 3,974,270 | 8/1976 | Kenkare | 424/66 |
| 4,053,581 | 10/1977 | Pader | 424/68 |
| 4,065,564 | 12/1977 | Miles | 424/68 |

FOREIGN PATENT DOCUMENTS

| | | | |
|---|---|---|---|
| 2453139 | 5/1975 | Fed. Rep. of Germany | 424/65 |
| 2510364 | 9/1975 | Fed. Rep. of Germany | 424/65 |
| 1485373 | 9/1977 | United Kingdom | 424/65 |

OTHER PUBLICATIONS

Sagarin, Cos., Sci & Tech. Intersci., N.Y. 1957, pp. 717-739.

*Primary Examiner*—Anna P. Fagelson

[57] ABSTRACT

Aerosol antiperspirant compositions are provided that are highly concentrated with respect to the active astringent salt, and capable of being dispensed from aerosol containers of the foam type at a low delivery rate, comprising, in combination, an astringent salt in an amount within the range from about 8 to about 30%; a liquefied propellant, or a mixture of liquefied propellants, each with a vapor pressure at 21° C. of at least 2.4 atmospheres absolute, having a low molecular weight, in an amount of at least 0.15 mole per atmosphere absolute pressure in the container at 21° C. per 100 g of composition; a nonvolatile miscible organic liquid in an amount within the range from about 0.1 to 30% by weight of the composition; a bulking agent in an amount within the range from about 0.1 to about 5% by weight of the composition; and a solid aliphatic carboxylic acid having from about fourteen to about twenty-two carbon atoms in a straight chain and in an amount within the range from about 0.1 to about 5% by weight of the composition to enhance adherence of the antiperspirant salt to the skin.

30 Claims, No Drawings

AEROSOL ANTIPERSPIRANT COMPOSITIONS WITH GOOD ADHERENCE TO THE SKIN

This application is a continuation-in-part of Ser. No. 724,425 filed Sept. 17, 1976 and now abandoned, which in turn is a continuation-in-part of Ser. No. 706,857 filed July 19, 1976, now abandoned, which in turn is a continuation-in-part of Ser. No. 554,388 filed Mar. 3, 1975, now U.S. Pat. No. 3,970,219 patented July 20, 1976, and of Ser. No. 670,913 filed Mar. 26, 1976, now U.S. Pat. No. 4,019,657 patented Apr. 26, 1977, as well as of Ser. No. 566,562 filed Apr. 9, 1975, Ser. No. 620,448 filed Oct. 7, 1975, and Ser. No. 628,283 filed Nov. 3, 1975, all three now abandoned.

Aerosol sprays are now widely used, particularly in the cosmetic, topical pharmaceutical and detergent fields, for delivery of an additive such as a cosmetic, pharmaceutical, or cleaning composition to a substrate such as the skin or other surface to be treated. Aerosol compositions are widely used as antiperspirants to direct the antiperspirant to the skin in the form of a finely divided spray.

The delivery of antiperspirants to the skin in a fine spray poses a difficult aerosol packaging problem. Aerosol antiperspirant compositions based on anhydrous propellant systems normally include antiperspirant, filler and other solid particles dispersed in a liquid vehicle, and the solid particles readily clog small valve orifices. On the other hand, if the orifices are large enough to avoid clogging, a coarse liquid spray with large droplets is formed, and there may be excessive drip at the nozzle. The material can even be squirted out in the form of a liquid stream, which rapidly runs off the surface on which it is deposited.

Much effort has accordingly been directed to the design of valves and valve delivery ports, nozzles or orifices which are capable of delivering finely-divided sprays, of which U.S. Pat. Nos. 3,083,917 and 3,083,918 patented Apr. 2, 1963, to Abplanalp et al, and No. 3,544,258, dated Dec. 1, 1970 to Presant et al, are exemplary. The latter patent describes a type of valve which is now rather common, giving a finely atomized spray, and having a vapor tap, which includes a mixing chamber provided with separate openings for the vapor phase and the liquid phase to be dispensed into the chamber, in combination with a valve actuator or button to the mechanical breakup type. Such valves provide a soft spray with a swirling motion. Another design of valves of this type is described in U.S. Pat. No. 2,767,023. Valves with vapor taps are generally used where the spray is to be applied directly to the skin, since the spray is less cold.

Marsh U.S. Pat. No. 3,148,127 patented Sept. 8, 1964 describes a pressurized self-dispensing package of ingredients for use as a hair spray and comprising isobutane or similar propellant in one phase and an aqueous phase including the hair setting ingredient. The isobutane is in a relatively high proportion to the aqueous phase, and is exhausted slightly before the water phase has been entirely dispensed. A vapor tap type of valve is used having a 0.030 inch vapor tap orifice, a 0.030 inch liquid tap orifice, and a 0.018 inch valve stem orifice, with a mechanical breakup button. There is no disclosure of the relative proportions of propellant gas to liquid phase being dispersed.

Rasbussier U.S. Pat. No. 3,260,421 patented July 12, 1966 describes an aerosol container for expelling an aqueous phase and a propellant phase, fitted with a vapor tap valve, and capillary dip tube. To achieve better blending of the phases before expulsion, the capillary dip tube is provided with a plurality of perforations 0.01 to 1.2 mm in diameter over its entire length, so that the two phases are admitted together in the valve chamber from the capillary dip tube, instead of the gas being admitted only through a vapor tap orifice, and the liquid through a dip tube as is normal. This propellant is blended in the liquid phase in an indeterminate volume in proportion to the aqueous phase in the capillary dip tube.

Presant et al in U.S. Pat. No. 3,544,258, referred to above, discloses a vapor tap valve having a stem orifice 0.018 inch in diameter, a vapor tap 0.023 inch in diameter with a capillary dip tube 0.050 inch in diameter. The button orifice diameter was 0.016 inch. The composition dispensed is an aluminum antiperspirant comprising aluminum chlorhydroxide, water, alcohol and dimethyl ether. The aluminum chlorhydroxide is in solution in the water, and there is therefore only one liquid phase. The dimensions of the orifices provided for this composition are too small to avoid clogging, in dispensing an aluminum antiperspirant composition containing dispersed astringent salt particles.

The vapor tap type of valve is effective in providing fine sprays. However, it requires a high porportion of propellant, relative to the amount of active ingredients dispensed per unit time. A vapor tap requires a large amount of propellant gas, because the tap introduces more propellant gas into each squirt of liquid. Such valves therefore require aerosol compositions having a rather high proportion of propellant. A high propellant proportion in undesirable, however. The fluorocarbon propellants are thought to be deleterious, in that thy are believed to accumulate in the stratosphere, where they may possibly interfere with the protective ozone layer there. The hydrocarbon propellants are flammable, and their proportion must be restricted to avoid a flame hazard. Moreover, both these types of propellants, and especially the fluorocarbons, have become rather expensive.

Another problem with such valves is that since they deliver a liquid propellant-aerosol composition mixture, and have valve passages in which a residue of liquid remains following the squirt, evaporation of the liquid in the valve passages after the squirt may lead to deposition of solid materials upon evaporation of liquids, and valve clogging. This problem has given rise to a number of expedients, to prevent the deposition of solid materials in a form which can result in clogging.

Consequently, it has long been the practice to employ large amounts of liquefied propellant, say 50% by weight or more, to obtain fine droplets of liquid sprays or fine powder sprays, and a rather small solids content, certainly less than 10%, and normally less than 5%. The fine sprays result from the violent boiling of the liquefied propellant after it has left the container. A case in point is exemplified by the dispersion-type aerosol antiperspirants, which contain 5% or less of astringent powder dispersed in liquefied propellant. It has not been possible to use substantially higher concentrations of astringents without encountering severe clogging problems.

There is considerable current interest in the substitution of compressed gases for fluorocarbons and hydrocarbons as propellants to obtain fine aerosol sprays. The reasons include the low cost of compressed gases, the flammability of liquefied hydrocarbon propellants, and the theorized hazard to the ozone layer of liquefied fluorocarbon propellants. Reasonably fine sprays of alcoholic solutions have been obtained using carbon dioxide at 90 psig and valving systems with very fine orifices. These orifices are so small that dispersed solids cannot be tolerated, and even inadvertent contamination with dust will cause clogging. Thus, a typical system will employ a 0.014 inch capillary dip tube, a 0.010 inch valve stem orifice, and a 0.008 inch orifice in a mechanical break-up actuator button. Only limited variations in delivery rates are possible, since the use of significantly larger orifices will coarsen the spray droplets.

Thus far, the art has not succeeded in obtaining fine aerosol sprays using aqueous solutions with compressed gases. The reasons for this are that water has a higher surface tension and a higher viscosity than alcohol (ethanol or isopropanol) and is also a poorer solvent for the compressed gases, particularly carbon dioxide, which is preferred. All of these factors adversely affect the break-up of droplets to form a fine spray.

Special designs of the delivery port and valve passages have been proposed, to prevent the deposit of solid materials in a manner such that clogging can result. U.S. Pat. No. 3,544,258 provides a structure which is especially designed to avoid this difficulty, for example. Such designs result however in a container and valve system which is rather expensive to produce, complicated to assemble because of the numerous parts, and more prone to failure because of its complexity.

In accordance with U.S. Pat. No. 3,970,219, of which this application is a continuation-in-part, aerosol containers are provided that are capable of delivering a foamed aerosol composition. The aerosol composition is foamed inside the aerosol container, and delivered through the valve of the aerosol container, as a foam or collapsed foam. Fine droplets are formed from the foamed aerosol compositions, due at least in part to collapse of thin foam cell walls into fine droplets. The propellant serves to foam the liquid within the container, forming a foamed aerosol composition, and propels from the container through the valve and delivery port both any foam and any droplets that form when the foam collapses.

With conventional aerosol containers, a substantial proportion of the propellant is in liquid form as the aerosol composition passes through the valve and delivery port. Propellant evaporates as the spray travels through the air, and it continues to evaporate after the spray has landed on a surface. The heat of vaporization is taken from the surface, and the spray consequently feels cold. This is wasteful of propellant, as is readily evidenced by the coldness of sprays from conventional aerosol containers. In contrast, in the invention of U.S. Pat. No. 3,970,219, the propellant is in gaseous form when expelled with the liquid. The propellant is not wasted, therefore, and since there is substantially no liquid propellant to take up heat upon vaporization, the spray is not cold.

The aerosol containers in accordance with the invention of U.S. Pat. No. 3,970,219 accordingly foam an aerosol composition therein prior to expulsion from the container, and then expel the resulting foamed aerosol composition. These aerosol containers comprise, in combination, a pressurizable container having a valve movable between open and closed positions, with a valve stem, and a foam-conveying passage therethrough, in flow connection with a delivery port; bias means for holding the valve in a closed position; and means for manipulating the valve against the bias means to an open position, for expulsion of aerosol composition foamed within the container via the valve passage and delivery port; means defining at least two separate compartments in the container, of which a first compartment is in direct flow connection with the valve passage, and a second compartment is in flow connection with the valve passage only via the first compartment, and porous bubbler means having through pores interposed between the first and second compartments with the through pores communicating the compartments, the pores being of sufficiently small dimensions to restrict flow of propellant gas from the second compartment therethrough and form bubbles of such gas in liquid aerosol composition across the line of flow from the bubbler to the valve, thereby to foam the aerosol composition upon opening of the valve to atmospheric pressure, and to expel foamed aerosol composition through the open valve.

U.S. Pat. No. 4,019,657, patented Apr. 26, 1977 provides another form of foam-type aerosol container, in which the aerosol composition therein is foamed prior to expulsion from the container, and then the resulting foamed areosol composition is expelled. These aerosol containers comprise, in combination, a pressurizable container having a valve movable between open and closed positions, with a valve stem, and a foam-conveying passage therethrough, in flow connection with a delivery port; bias means for holding the valve in a closed position; and means for manipulating the valve against the bias means to an open position for expulsion via the valve passage and delivery port of aerosol composition foamed within the container; means defining at least two separate compartments in the container, of which a first compartment has a volume of at least 0.5 cc and is in direct flow connection with the valve passage, and a second compartment is in flow connection with the valve passage only via the first compartment; at least one first liquid tap orifice having a diameter within the range from about 0.012 to about 0.2 cm and communicating the first and another compartment for flow of liquid aerosol composition into the first compartment, and of sufficiently small dimensions to restrict flow of liquid aerosol composition therethrough; the ratio of first compartment volume/first orifice diameter being from about $10/x$ and preferably from about $20/x$ to about $400/x$, and preferably about $200/x$, where x is 1 when the orifice length is less than 1 cm, and 2 when the orifice length is 1 cm or more; at least one second gas tap orifice having a total cross-sectional open area within the range from about $7 \times 10^{-6}$ to about $20 \times 10^{-4}$ in$^2$ ($4 \times 10^{-5}$ to $1.3 \times 10^{-2}$ cm$^2$), a single orifice having a diameter within the range from about 0.003 to about 0.05 inch (0.007 to 0.13 cm) and communicating the first and second compartments for flow of propellant gas into the first compartment from the second compartment therethrough, and of sufficiently small dimensions to restrict flow of propellant gas and form bubbles of such gas in liquid aerosol composition across the line of flow thereof to the valve, thereby to foam the aerosol composition upon opening of the valve to atmospheric pressure, and to expel the foamed aerosol composition through the open valve.

The advantages of foaming the aerosol composition within the container are twofold. Because the propellant is in gaseous form (having been converted to gas in the foaming) there is no liquid propellant to expel, so all propellant is usefully converted into gas, for propulsion and foaming, before being expelled. Because the foamed liquid aerosol composition has a higher volume than the liquid composition, and the expulsion rate is in terms of volume per unit time, less liquid is expelled per unit time. Thus, in effect, the liquid is expelled at a lower delivery rate, which conserves propellant per unit squirt, and means a higher active concentration must be used, to obtain an equivalent delivery rate of active ingredient. Also, since there is less liquid, there is a negligible clogging problem, even at a two or three times higher active concentration.

The disadvantage of foaming however is the need to provide space for the foaming to take place, which requires either a larger container or a smaller unit volume of composition per container.

U.S. patent applications Ser. Nos. 706,857, filed July 19, 1976, and 757,414, filed Jan. 6, 1977, show that a low delivery rate can be achieved without the necessity of providing a foam chamber or space within the aerosol container, if the volume proportion of gas to liquid in the blend dispensed from the container is within the range from about 10:1 to about 40:1, and preferably within the range from about 15:1 to about 30:1, the gas volume being calculated at its pressure within the container. This is a sufficient proportion of gas to liquid to form a foam, such as is formed and dispensed from the foam type aerosol containers of U.S. Pat. Nos. 3,970,219 and 4,019,657, referred to above, and a very much higher proportion of gas to liquid than has previously been blended with the liquid for expulsion purposes in coventional aerosol containers, such as the vapor tap containers of the Presant U.S. Pat. No. 3,544,258 referred to above. At such higher proportions of gas to liquid, the formation of foam is possible, and even probable, despite the small volume of the blending space provided, but foam formation, if it occurs, is so fleeting, having a life of at most a fraction of a second, that a foam cannot be detected by ordinary means, due to the small dimensions of the open spaces in which it may exist, i.e., the blending space and valve passages, and the shortness of the delivery time from blending of gas and liquid to expulsion. However, the proportion of gas to liquid in the blend that is expelled can be determined, and when the proportion in in excess of 10:1, the delivery rate of liquid from the aerosol container is very low, and thus, the objective of the invention is achieved. Whether or not a foam is formed is therefore of no significance, except as a possible theoretical explanation of the phenomenon.

Accordingly, Ser. Nos. 706,857 and 757,414 provide a process for dispensing a spray containing a low proportion of liquid, with a high proportion of propellant in gaseous form, by blending gas and liquid within the aerosol container prior to expulsion at a ratio of gas: liquid within the range from about 10:1 to about 40:1, and preferably from about 15:1 to about 30:1, with the result that a blend containing this low proportion of liquid and high proportion of gas is expelled from the container, and the proportion of liquid composition expelled per unit time correspondingly reduced.

The aerosol container disclosed in Ser. Nos. 706,857 and 757,414 comprises, in combination, a pressurizable container having a valve movable between open and closed positions, a valve stem, and a delivery port; a valve stem orifice in the valve stem in flow connection at one end with a blending space and at the other end with an aerosol-conveying valve stem passage leading to the delivery port; the valve stem orifice having a diameter within the range from about 0.50 to about 0.65 mm; bias means for holding the valve in a closed position; means for manipulating the valve against the bias means to an open position for expulsion of aerosol composition via the valve stem orifice to the delivery port; wall means defining the blending space and separating the blending space from liquid aerosol composition and propellant within the container; at least one liquid tap orifice through the wall means, having a cross-sectional open area within the range from about 0.4 and 0.8 $mm^2$ for flow of liquid aerosol composition into the blending space; at least one vapor tap orifice through the wall means, having a cross-sectional open area within the range from about 0.3 to about 0.5 $mm^2$ for flow of propellant into the blending space; the ratio of liquid tap orifice to vapor tap orifice cross-sectional open area being within the range from about 1.4 to about 2.3; the open areas of the liquid tap orifice and vapor tap orifice being selected within the stated ranges to provide a volume ratio of propellant gas: liquid aerosol composition within the range from about 10:1 to about 40:1, thereby limiting the delivery rate of iquid aerosol composition from the container when the valve is opened.

In the special case where the liquid tap orifice is a capillary dip tube the cross-sectional open area thereof is within the range from about 0.8 to about 1.8 $mm^2$, for flow of liquid aerosol composition into the blending space, and at least one vapor tap orifice through the wall means has a cross-sectional open area within the range from about 0.3 to about 0.6 $mm^2$ for flow of propellant gas into the blending space; and the ratio of capillary dip tube to vapor tap orifice cross-sectional open area is within the range from about 1.2 to about 3.2.

The controlling orifices to achieve the desired proportion of gas and liquid in the blend dispensed from the container are the vapor tap orifice, the liquid tap orifice (or in the case of a capillary dip tube, the capillary dip tube), and the valve stem orifice. The open areas of these orifices and the ratio of liquid tap orifice to vapor tap orifice open area should be controlled within the stated ranges.

The valve delivery system normally includes, in addition to the valve stem orifice, an actuator orifice at the end of the passage through the actuator of the valve. The valve delivery system from the blending chamber through the valve stem and actuator to the delivery port thus includes, in flow sequence towards the delivery end, the valve stem orifice, the valve stem passage, the actuator passage, and the actuator orifice. The controlling orifice in this sequence is the valve stem orifice, and the actuator orifice will normally have a diameter the same as or greater than the valve stem orifice.

Because of the high proportion of propellant gas to liquid in the compositions dispensed from thse types of aerosol containers, special problems arise in the formulation of aerosol compositions that can be fully expelled from the aerosol container before the supply of propellant gas is exhausted, without undue mistiness or dustiness, and deposit on the skin a composition which adheres well, and has good antiperspirant efficiency. For delivery of the same amount of astringent salt per unit time or squirt, these containers require that the aerosol formulation contain an unusually high proportion of astringent salt, in excess of 8%, and ranging as high as 10 to 20%, and more. Since the usual anhydrous dispersion-type aerosol antiperspirant compositions contain dispersed solids, the resulting high proportion of solid to liquid poses special problems of dustiness and adherence to the skin, since the proportion of solid material is greatly in excess of the normal proportion, when the astringent salt is in the usual low concentration of less than 5%.

Moreover, the expulsion of such a large proportion of gas to liquid tends to reduce the liquid to very fine droplets, which form relatively stable aerosols in the air, and tend not to be deposited on the skin, but instead remain suspended in the vicinity of the aerosol can applicator. This not only wastes astringent salt, but also poses a hazard to the user, who can inhale such aerosols, as well as leading to deposits of the material later on, in other parts of the room.

The expulsion of the aerosol composition from the container with a high proportion of gas requires a sufficient quantity of low molecular weight propellant at a sufficiently high vapor pressure to provide both the requisite volume of gas and a sufficient pressure to forcibly expel all of the contents of the container.

A conventional dispersion-type antiperspirant composition in a conventional aerosol container usually contains by weight about 10% nonvolatile components, comprising finely divided solids and oils, and about 45% each of Propellants 11 and 12. Since the proportion of gas to liquid expelled is quite low, the proportions of the ingredients remaining in the container and the internal pressure remain fairly constant as the container is used, and all of the contents can be expelled.

However, if from 10 to 40 volumes of gas were expelled, per volume of liquid, the high vapor pressure Propellant 12 would be used up first, since it would provide practically all of the gas expelled. After it was all gone, about one-third of the original weight of the contents of the container would remain, and could not be expelled by the remaining Propellant 11. The individual propellants of the propellant mixture are as important as the mixture itself.

In order to expel from 10 to 40 volumes of gas per volume of liquid, propellants are employed with a vapor pressure at 21° C. of at least 2.4 atmospheres absolute, in an amount of at least 0.15 moles, and preferably at least 0.25 mole, per atmosphere absolute pressure in the container at 21° C., per 100 g of composition.

The importance of this low volatility is illustrated by the following Examples. In these Examples, the compositions consist of 20 g of finely divided solids, and nonvolatile oils, and 80 g of propellant. The vapor-pressure depression due to the oils is small, and is ignored.

A propellant mixture of 40 g each of Propellants 11 and 12 has a pressure of 3.6 atmospheres absolute at 21° C. Only Propellant 12 has a vapor pressure at 21° C. of at least 2.4 atmospheres absolute, and 40 g of this propellant equals 0.33 mole. This value divided by 3.6 atmospheres equals 0.09 mole per atmosphere absolute per 100 g of composition. This amount is insufficient to expel 20 g of solids and oils from the container.

If the propellant consisted entirely of 80 g of Propellant 12, it would comprise 0.66 mole of propellant, with a vapor pressure at 21° C. of 5.8 atmospheres absolute. This corresponds to 0.11 mole per atmosphere absolute per 100 g of composition, which is also insufficient to expel all of the solids and oils of the composition.

If the propellant consisted of 80 g of isobutane, it would comprise 1.38 moles of propellant at a pressure of 3.1 atmospheres absolute at 21° C., corresponding to 0.45 mole per atmosphere absolute per 100 g of composition. This is sufficient to expel 20 g of solids and oils.

If a propellant mixture is used consisting of 40 g of isobutane and 20 g each of Propellants 11 and 12, the calculated internal pressure is 3.23 atmospheres absolute at 21° C. The propellant mixture comprised 0.69 mole of isobutane plus 0.165 mole of Propellant 12 for a total of 0.855 mole of propellants having a vapor pressure of at least 2.4 atmospheres absolute. Then 0.855/3.23 equals 0.26 mole propellant per atmosphere absolute pressure per 100 g of composition.

The following Table shows the number of moles of propellant per atmosphere absolute pressure of the propellant at 21° C. for 80 g of propellant. All of the propellants shown in the table have a vapor pressure of at least 2.4 atmospheres absolute at 21° C.

TABLE I

| | Mole/atmosphere absolute |
|---|---|
| Propane | 0.22 |
| Cyclopropane | 0.31 |
| Isobutane | 0.45 |
| Dimethyl ether | 0.34 |
| Chlorodifluoromethane | 0.10 |
| Dichlorodifluoroethane | 0.11 |
| 1-Chloro-1,1-difluoroethane | 0.26 |
| 1,1-Difluoroethane | 0.23 |

It will be noted that the maximum vapor pressure for the liquefied propellant is limited by the requirement concerning the moles of propellant per atmosphere absolute pressure. Thus, propane, with a lower molecular weight than isobutane, provides less than half the number of moles per unit pressure. The same quantity of ethane, with a molecular weight of only 30, and a vapor pressure of 38 atmospheres absolute, provides only 0.07 mole per atmosphere absolute.

In accordance with the invention, aerosol antiperspirant compositions are provided that are highly concentrated with respect to the active astringent salt, and capable of being dispensed from aerosol containers of the foam type at a low delivery rate, comprising, in combination, an astringent salt in an amount within the range from about 8 to about 30%; a liquefied propellant, or a mixture of liquefied propellants, each with a vapor pressure at 21° C. of at least 2.4 atmospheres absolute and having a low molecular weight; a nonvolatile miscible organic liquid in an amount within the range from about 0.1 to 30% by weight of the composition; a bulking agent in an amount within the range from about 0.1 to about 5% by weight of the composition; and a solid aliphatic carboxylic acid having from about fourteen to about twenty-two carbon atoms in a straight chain in an amount within the range from about 0.1 to about 5% by weight of the composition to enhance adherence of the antiperspirant salt to the skin.

Such aerosol antiperspirant compositions are especially effective when capable of being dispensed from aerosol containers of the foam type at a low delivery rate in a propellant gas:liquid ratio within the range from about 10:1 to about 40:1 with the liquefied propellant in an amount of at least 0.15 mole per atmosphere absolute pressure at 21° C. per 100 g of composition to generate an expelled gas:liquid ratio within the range from about 10:1 to about 40:1, and in such compositions the solid saturated aliphatic carboxylic acid having from about fourteen to about twenty-two carbon atoms in a straight chain and in an amount within the range from about 0.1 to about 5% by weight of the composition improves adherence of the antiperspirant salt to the skin, but the solid saturated aliphatic carboxylic acid is also useful in general to improve adherence of the antiperspirant salt in aerosol antiperspirant compositions as broadly defined above.

Dispersion-type aersol antiperspirant compositions in general are composed of an astringent salt in combination with a nonvolatile miscible organic liquid such as isopropyl myristate to improve adherence of the astringent salt to the skin. This type of formulation is described in many patents, including, for example, U.S. Pat. Nos. 3,968,203, patented July 6, 1976 to Spitzer et al, 3,725,540, patented Apr. 3, 1973 to Wahl, 3,903,258, patented Sept. 2, 1975 to Siegal, and 3,959,459, patented May 25, 1976 to Curry. These liquids are frequently referred to as nonvolatile oils, as liquid carriers, and as emollients, and they are generally used within the range from about 1 to about 10% of the composition.

The function of the nonvolatile liquid is to adhere the astringent salt to the skin. However, these oils have an insufficient bonding capacity to be more moderately effective in adhering the astringent salt to the skin.

Accordingly, as an adherence-promoting agent more effective for this purpose, there is included in the compositions of the invention a solid aliphatic carboxylic acid having from about fourteen to about twenty-two carbon atoms in a straight chain. The straight chain saturated aliphatic acids are satisfactory. The solid acid can have more than one carboxylic acid group, and it can also contain other groups, such as hydroxyl, amido, ether and carboxylic acid ester groups.

Thus, the class of solid aliphatic straight-chain carboxylic acids which can be employed as adherence-promoting agents in the compositions of the invention include the aliphatic carboxylic acids having from about fourteen to about twenty-two carbon atoms, from one to four carboxylic acid groups, and, optionally, from one to four hydroxyl and/or ester or ether or amido groups.

Exemplary solid aliphatic carboxylic acids include palmitic acid, myristic acid, stearic acid, behenic acid and margaric acid, as well as solid commercially available fatty acid mixtures derived from natural fats and oils such as coconut oil fatty acids and tallow fatty acids. The liquid acids of corresponding chain length, such as oleic acid, linoleic acid, linolenic acid, ricinoleic acid, isostearic acid (the commercial liquid grade of stearic acid), and the liquid fatty acid mixtures, for example, tung oil fatty acids, safflower oil fatty acids, corn oil fatty acids, cottonseed oil fatty acids, fish oil fatty acids, whale oil fatty acids, sunflower oil fatty acids, sesame seed oil fatty acids, linseed oil fatty acids, and castor oil fatty acids, cannot be used.

Examples of solid aliphatic carboxylic acids containing other groups include stearoyl sarcosine and stearoyl lactylate. The sarcosines contain an amidomethyl group. The lactylates are prepared by esterifying one mole of fatty acid with two or more moles of lactic acid, and thus contain two or more ester groups.

The carboxylic acids may be used in any mixture or combination.

The amount of solid carboxylic acid based on the astringent salt is within the range from about 1 to about 15%.

The amount of carboxylic acid that is employed is selected in accordance with its solubility in the liquid phase of the composition, and according to the specific carboxylic acid, or mixture of carboxylic acids, that is employed, the amount of astringent salt present, and the particle size of the astringent salt.

In general, the amount of nonvolatile liquid should not exceed about 200% by weight of the astringent salt. Any of the nonvolatile liquids known in the art can be used.

The term "nonvolatile" means that the liquid will not volatilize during the time the composition is on the skin and before it is adsorbed. This usually requires only a few minutes. Thus, the term "nonvolatile" does not exclude materials that are slowly volatile and require a long time to evaporate fully, such as the volatile silicones. These are generally poly dimethyl siloxanes of low viscosity, about 2 or 3 centistokes at 25° C.

Other suitable examples include fatty acid esters of polyalkylene glycols wherein the fatty acid contains from about two to about twenty carbon atoms, and from about two to about two hundred alkylene glycol units per fatty acid molecule; fatty acid esters of aliphatic alcohols where the esters contain from about twelve to about twenty-six carbon atoms, such as ethyl laurate, isopropyl myristate, isopropyl palmitate, isopropyl behenate, decyl acetate, behenyl butyrate, hexadecyl acetate, decyl decanoate, methyl oleate, lauryl laurate, and oleyl acetate; esters containing multiple ester groups such as those disclosed in British patent specification No. 1,353,914, that is, multiple ester organic compounds of from about twelve to about sixteen carbon atoms having a ratio of ester groups to carbon atoms of from 0.125 to 0.214 and having a solubility in water of 0.0005% to 0.1% at 30° C., examples being di-n-octyl-n-decyl phthalate, di-n-octyl phthalate, di-n-hexyl phthalate, di-n-butyl phthalate, diethyl sebacate, diisopropyl adipate, and ethyl ethoxycarbonyl phthalate

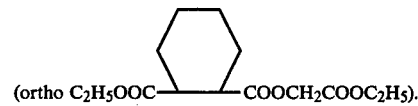

(ortho C₂H₅OOC—COOCH₂COOC₂H₅).

Liquids more hydrophilic than these esters include polyethylene glycol monolaurate and Fluid AP, a product of the Union Carbide Company.

Among these various liquid carboxylic acid esters, those having from about twelve to about twenty-six carbon atoms are preferred. As described above, they can be either aliphatic or aromatic and can contain either one or more ester groups. Especially preferred are the esters, e.g., di-n-butyl phthalate, diethyl sebacate, diisopropyl adipate, ethyl ethoxycarboxyl phthalate, and Fluid AP.

The propellant can be a hydrocarbon, a halocarbon, or a mixture thereof, having a vapor pressure of at least 2.4 atmospheres absolute at 21° C.

Exemplary hydrocarbon propellants within the above class include isobutane, cyclopropane, and propane. Isobutane is particularly preferred, because a given weight will provide a large number of moles of propellant per unit vapor pressure. It is generally preferred that the propellant mixture in the compositions of the invention contain at least 20% by weight of isobutane, and that the proportion of isobutane by weight of the entire composition be at least 15%. Mixtures of isobutane with propane or cyclopropane are preferred.

Exemplary halocarbon propellants include 1,1-difluoroethane and 1-chloro-1,1-difluoroethane. These can be used alone or admixed with hydrocarbon propellants or other halocarbon propellants. The latter include chlorodifluoromethane and dichlorodifluoromethane. Combinations of one or more of the latter halocarbon propellants with isobutane are especially preferred.

Dimethylether can also be used, alone or in admixture with hydrocarbon or halocarbon propellants. However, it has a greater toxicity than any of the propellants mentioned above.

Nonflammable halocarbons with a low vapor pressure can be employed to reduce the flammability of hydrocarbon and halocarbon propellants. Examples of such halocarbons include methylene chloride, 1,1,1-trichloromethane, trichlorofluoromethane, dichlorofluoromethane, and 1,2-dichlorotetrafluoroethane.

As an optional feature, as described and claimed in U.S. Pat. No. 4,152,416, patented May 1, 1979, excessive dustiness or mistiness can be avoided by including in the composition a synthetic polymer gum that is soluble in the liquid phase of the composition.

The term "gum" is used to refer to a material that has a viscosity within the range from about 500,000 to about 100,000,000 centistokes at 25° C., because it is either a rubbery or soft solid or is slowly flowable, as opposed to a rigid solid, which is not flowable, or a liquid, which is too flowable.

The polymer gums are either soft or rubbery solids, or highly viscous materials, flowable under stress, but are too slowly flowable to be properly described as oils or liquids. Any synthetic polymer having a viscosity within this range can be used provided it is soluble in the liquid phase (including the propellant and nonvolatile liquid). The function of the polymer gum is to increase the viscosity of the liquid phase. Silicone gums, and especially silicone polymers of the dimethyl polysiloxane type, and acrylic polymers are available within this range, and are preferred. Hydrocarbon polymer gums can also be used.

An approximate empirical relationship between the viscosity of linear silicone gum polymers and their average molecular weight is given in Kirk-Othmer, *Encyclopedia of Chemical Technology*, Interscience Publishers 18 226 (Second Edition, 1969):

log (viscosity in centistokes at 25° C.)=$(1.00+0.0123 M_n^{\frac{1}{2}})$ where $M_n$ is average molecular weight.

This relationship suggests that useful linear silicone gums fall within the molecular weight range of about 140,000 to 350,000. However, branched-chain silicone gums are also useful, and have higher molecular weights at the same viscosity, depending on the degree of branching. Highly branched silicone gums have molecular weights extending to about 2 million.

Particularly useful are silicone gums of the dimethyl polysiloxane type. These may have other groups attached, such as phenyl, vinyl, cyano, or acrylic, but the methyl groups should be in a major proportion.

Silicone polymers having a viscosity below about 100,000 centistokes (molecular weight below about 100,000) at 25° C. are not gums; they are oils, and are ineffective in reducing a tendency towards stable aerosol formations, i.e., mistiness and dustiness at 10:1 to 40:1 gas:liquid ratios.

Acrylic polymer gums which can be used include octyl methacrylate, octadecyl methacrylate, butyl acrylate, isobutyl acrylate, copolymers of butyl acrylate and isobutyl acrylate, copolymers of higher alkyl methacrylate copolymers of butyl methacrylate and butyl acrylate; and copolymers of butyl methacrylate and isobutyl acrylate; and copolymers of any one or more of these with acrylonitrile, isoprene, isobutylene or butadiene. These gums can have a molecular weight within the range from about 30,000 to about 2,000,000, but the molecular weight is not critical.

Hydrocarbon polymer gums that can be used include polyisobutylene, polyisoprene, isobutylene-isoprene copolymers, and chloroisobutylene-isoprene copolymers and polybutadiene. Hydrocarbon polymer gums can have a molecular weight within the range from about 30,000 to about 2,000,000, but the molecular weight is not critical.

The amount of polymer gum is within the range from about 0.05 to about 5% and preferably from about 0.1 to about 2%, by weight of the composition. The higher the molecular weight or viscosity of the polymer, the less of it is required to reduce mistiness.

It is important that the polymer gum be soluble in the liquid phase of the composition. It is advantageous but not essential that the polymer be soluble in the nonvolatile oil component of the composition. If the polymer is not soluble, and is of a rubbery or soft solid consistency, residues in the valve or actuator button may have a tendency to cause clogging. This can be avoided by adding a lubricant. Any conventional lubricant can be used. Silicone oils are lubricants with silicone gums, for example. Some nonvolatile organic liquids are lubricants.

As the astringent salt, any antiperspirant aluminum or zirconium salt can be employed in the antiperspirant compositions of the invention.

Suitable antiperspirant aluminum and/or zirconium salts are any of those well known in the art, whether soluble or insoluble in the antiperspirant compositions of the invention. Generally, these are acidic inorganic salts of aluminum and zirconium. Examples of aluminum and zirconium salts are aluminium chlorhydroxide, aluminum chloride, aluminum sulfate, aluminum oxychloride, aluminum oxysulfate, zirconyl chloride, zirconyl hydroxychloride, and zirconium oxychloride.

Many inorganic-organic mixtures and complexes are also known astringent salts, such as zirconium salt/amine/and amino acid complexes, Siegel U.S. Pat. No. 3,407,254; zirconium salt/aluminum chlorhydroxide/glycol complexes, Jones et al U.S. Pat. No. 3,405,153; aluminum chlorhydroxide/glycol complexes, Jones et al U.S. Pat. No. 3,402,932; aluminum chlorhydroxide/zirconyl hydroxychloride complexes; and aluminum hydroxide/zirconyl hydroxychloride/amino acid complexes. Also useful are the aluminum and zirconium salts complexed with polyols such as propylene glycol.

As the antiperspirant aluminum and/or zirconium salt, in accordance with the invention, aluminum chlorhydroxide and zirconium chlorhydroxide, and mixtures of aluminum chlorhydroxide and zirconium chlorhydroxide, with or without aluminum chloride or sulfate, are preferred. Aluminum chloride and sulfate can also be used, but these are less preferred.

In order to prevent caking or settling out of the astringent salt in the compositions of the invention, so that it cannot be dispensed from the aerosol container, a bulking agent can be incorporated. This is a finely divided particulate material, inert and insoluble in the liquids present, having a particle size below 10 microns in diameter, and includes colloidal silica and hydrophobic clays.

The colloidal silica is preferably a pyrogenic silica, but other types of silica particles of colloidal sizes may be employed. The colloidal silica will normally be of particle size less than 100 mμ, preferably averaging less than 50 mμ in diameter. Among the more preferred pyrogenic silicas the diameters will be in the 2 to 20 mμ range. A preferred pyrogenic silica, sold by Cabot Corporation, Boston, Massachusetts, as Cab-O-Sil M-5 (Cab-O-Sil is a trademark), has an ultimate particle diameter of about 11 mμ while the corresponding H-5 grade has a diameter of about 7 mμ. The surface areas of the pyrogenic colloidal silicas and other colloidal silicas having an average particle size less than one micron are exceptionally great, often resulting from about 50 to 500 square meters per gram, leading to desirable thickening, suspending and covering properties. The particles are also of generally spherical shape.

Examples of hydrophobic treated clays that swell in inorganic solvents include hydrophobic bentonite, e.g. Bentone (Registered Trade Mark) 38, and the other Bentones, which are bentonite treated with a hydrophobic cationic material such as ditallowalkyldimethylammonium chloride.

In addition to the propellant, an organic solvent can be added the solvent reduces the vapor pressure and the viscosity of the composition as well as the oiliness of the deposit on the skin. Suitable solvents for this purpose are pentane, hexane, trichlorotrifluoroethylene, trichlorofluoromethane, dichlorofluoromethane, and methylene chloride. Many hydrocarbon and halocarbon liquefied propellants also serve the same purpose, however, if they remain in the deposit on the skin.

In addition to the above-mentioned ingredients, there can be employed the customary adjuncts of aerosol antiperspirant compositions, such as perfumes, bactericides, fungicides, emollients, and other skin-treating materials.

The aerosol compositions in accordance with the invention can be defined by the following general formulation ranges:

|  | Parts Overall By Weight | Preferred Parts By Weight |
| --- | --- | --- |
| Antiperspirant Salt | 8 to 30 | 8 to 15 |
| Bulking agent | 0.1 to 5 | 0.2 to 2 |
| Nonvolatile liquid | 1 to 30 | 1.2 to 20 |
| Carboxylic acid | 0.1 to 5 | 0.1 to 1.5 |
| Polymer gum | 0 to 5 | 0 to 2 |
| Propellant > 2.4 atmos. abs. | 30 to 90 | 45 to 89 |
| Other liquefied propellants or volatile solvents | 0 to 60 | 0 to 44 |

The preferred polymer gum is a silicone gum with a viscosity in the range of 500,000 to 100 million centipoise at 25° C., corresponding to a molecular weight in the range of 140,000 to 2 million.

The following Examples in the opinion of the inventors represent preferred embodiments of their invention. In the Examples, in addition to the formulations, the dimensions of the important components and the type of aerosol container in which such a composition is best used are also given.

EXAMPLE 1

An aerosol antiperspirant composition was prepared having the following formulation:

|  | Parts By Weight |
| --- | --- |
| Aluminum chlorhydroxide | 10.3 |
| Stearic acid (solid, titer 65° C.) | 2.5 |
| Isopropyl myristate | 7.8 |
| Silicone gum, 2 million centistokes at 25° C. (polydimethyl siloxane) | 1.4 |
| Cab-O-Sil silica | 1.0 |
| Isobutane | 65.0 |
| Propane | 12.0 |

The colloidal silica, stearic acid, and isopropyl myristate were placed in a Waring Blendor, and mixed at high speed for 5 minutes. The dispersion was then mixed with the aluminum chlorhydroxide and silicone gum, and homogenized.

The composition was then filled into an aerosol container of the type shown in FIGS. 1, 1A and 2 of Ser. No. 706,857, filed July 19, 1976, having the dimensions shown below, and pressurized with the isobutane-propane mixture.

|  | Internal Diameter | |
| --- | --- | --- |
|  | Inch | mm |
| Valve stem orifice | 0.020 | 0.51 |
| Bubbler orifice | 0.030 | 0.76 |
| Capillary dip tube | 0.040 | 1.0 |
| Actuator orifice | 0.020 | 0.51 |

In a two-second spray application, there was expelled 0.8 g of antiperspirant composition, which deposited on the skin 0.060 g of astringent salt. The composition was quite effective in inhibiting perspiration for one day.

EXAMPLE 2

An aerosol antiperspirant composition was prepared having the following formulation:

|  | Parts By Weight |
| --- | --- |
| Aluminum chlorhydroxide | 8.4 |
| Stearic acid, solid, triple pressed (titer 55° C.) | 0.2 |
| Decyl oleate | 8.1 |
| Butyl 077[1] | 1.0 |
| Bentone 38 bentonite clay | 0.3 |
| Isobutane | 18.0 |
| Trichlorofluoromethane | 32.0 |
| Dichlorofluoromethane | 32.0 |

[1] Exxon Chemicals, isobutylene-isoprene copolymer gum, viscosity average molecular weight 425,000 (Flory)

The hydrophobic bentonite clay was combined with the decyl oleate, in which the stearic acid had been dissolved, and mixed in a Waring Blendor at high speed for 5 minutes, then combined with the aluminum chlorhydroxide and homogenized. The polymer gum was dissolved in the trichlorofluoromethane at 0° C. by stirring in a closed container for 2 hours. The dispersion was cooled and combined with the polymer solution.

The composition was then poured into an aerosol container of the type shown in FIGS. 1, 1A and 2 of Ser. No. 706,857, filed July 19, 1976. The composition was then pressurized by the addition of the isobutane, and dichlorofluoromethane.

The aerosol container has the following dimensions:

|  | Internal Diameter | |
|---|---|---|
|  | Inch | mm |
| Valve stem orifice | 0.20 | 0.51 |
| Bubbler orifice | 0.025 | 0.64 |
| Capillary dip tube | 0.040 | 1.0 |
| Actuator orifice | 0.020 | 0.51 |

A two-second application from the container expelled 1.3 g of antiperspirant composition, and deposited 0.10 g of aluminum chlorhydroxide on the skin. The composition was effective for one day in inhibiting perspiration.

EXAMPLE 3

An aerosol antiperspirant composition was prepared having the following formulation:

|  | Parts By Weight |
|---|---|
| Aluminum chlorhydroxide | 13.0 |
| Palmitic acid (titer 56° C.) | 0.4 |
| Diisopropyl adipate | 5.0 |
| Isopropyl myristate | 5.4 |
| Silicone gum, 2 million centistokes (polydimethyl siloxane) | 2.0 |
| Cab-O-Sil silica | 1.2 |
| Isobutane | 73.0 |

The palmitic acid was dissolved in the mixture of diisopropyl adipate and isopropyl myristate. The collodial silica was added and mixed in a Waring Blendor at high speed for 5 minutes. The dispersion was then combined with the aluminum chlorhydroxide and silicone gum and homogenized. The composition was filled into an aerosol container of the type shown in FIGS. 1 and 2 of U.S. Pat. No. 4,019,657 patented Apr. 26, 1977, having the dimensions shown below and pressurized with isobutane.

|  | Internal Diameter | |
|---|---|---|
|  | Inch | mm |
| Valve stem orifice | 0.025 | 0.64 |
| Foam chamber, height × diameter | 1.0 × 0.3 | 25 × 8 |
| Bubbler orifice | 0.040 | 1.0 |
| Capillary dip tube | 0.040 | 1.0 |
| Actuator orifice | 0.025 | 0.64 |

A two-second application of the composition expelled 1.0 g of spray, and deposited on the skin 0.065 g aluminum chlorhydroxide. This was effective to inhibit perspiration for one day.

EXAMPLE 4

An aerosol antiperspirant composition was prepared having the following formulation:

|  | Parts by Weight |
|---|---|
| Aluminum chlorhydroxide | 8.0 |
| Myristic acid | 0.5 |
| Isopropyl myristate | 13.1 |
| Bentone 38 bentonite clay | 0.4 |
| 1-chloro-1,1-difluoroethane | 70.0 |
| Chlorodifluoromethane | 8.0 |

The hydrophobic bentonite clay Bentone 38 was mixed with the isopropyl myristate and myristic acid in a Waring Blendor at high speed for five minutes. The dispersion was then combined with the aluminum chlorhydroxide and homogenized.

The dispersion was then cooled to 15° C. and combined with 20 parts of 1, chloro-1,1-difluoroethane at the same temperature in a closed container, and stirred for two hours.

The composition was then filled into aerosol containers of the type shown in FIGS. 1, 1A and 2 of Ser. No. 706,857 filed July 19, 1976. The composition was then pressurized by the addition of the remainder of the 1-chloro-1,1-difluoroethane and the chlorodifluoromethane.

The aerosol container had the following dimensions:

|  | Internal Diameter | |
|---|---|---|
|  | Inch | mm |
| Valve stem orifice | 0.020 | 0.51 |
| Bubbler orifice | 0.035 | 0.89 |
| Capillary dip tube | 0.040 | 1.0 |
| Actuator orifice | 0.025 | 0.64 |

In a two-second application of the composition there was expelled 1.1 g of composition, which deposited on the skin 0.080 g aluminum chlorhydroxide. This was effective to inhibit the development of perspiration odor for one day.

EXAMPLE 5

An aerosol antiperspirant composition was prepared having the following formulation:

|  | Parts By Weight |
|---|---|
| Aluminum chlorhydroxide | 9.0 |
| Stearic acid(solid), titer 55° C.) | 0.3 |
| Decyl oleate | 9.7 |
| Cab-O-Sil silica | 1.0 |
| Propane | 13.0 |
| Isobutane | 67.0 |

The colloidal silica, stearic acid, and decyl oleate were placed in a Waring Blender and mixed at high speed for five minutes. The dispersion was then mixed with the aluminum chlorhydroxide and homogenized.

The composition was then filled into an aerosol container of the type shown in FIGS. 1 and 2 of U.S. Pat. No. 4,019,657 patented Apr. 26, 1977, having the dimensions shown below, and pressurized with the isobutane-propane mixture.

|  | Internal Diameter | |
|---|---|---|
|  | Inch | mm |
| Valve stem orifice | 0.025 | 0.64 |
| Foam chamber, height × diameter | 1.0 × 0.3 | 25 × 8 |
| Bubbler orifice | 0.040 | 1.0 |
| Capillary dip tube | 0.040 | 1.0 |
| Actuator orifice | 0.025 | 0.64 |

In a two-second spray application, there was expelled 1.1 g of antiperspirant composition, which deposited on the skin 0.080 g of astringent salt. The composition was quite effective in inhibiting perspiration for one day.

EXAMPLE 6

An aerosol antiperspirant composition was prepared having the following formulation:

|  | Parts By Weight |
| --- | --- |
| Aluminum chlorhydroxide | 8.0 |
| Myristic acid (titer 53° C.) | 0.8 |
| Isopropyl myristate | 12.0 |
| Silicone gum 10-20 million centistokes (polydimethyl siloxane) | 0.4 |
| Cab-O-Sil silica | 0.8 |
| Propane | 12.0 |
| Isobutane | 66.0 |

The silicone gum was dissolved in 2 parts of the isopropyl myristate by heating while stirring. The colloidal silica was added to a solution of myristic acid in the remainder of the isopropyl myristate and the dispersion was mixed in a Waring Blendor at high speed for 5 minutes, then combined with the aluminum chlorhydroxide and the gum solution and homogenized.

The composition was then poured into an aerosol container of the type shown in FIGS. 3 and 4 of Ser. No. 706,857 filed July 19, 1976. The composition was then pressurized by the addition of the isobutane and propane.

The aerosol container had the following dimensions:

|  | Internal Diameter | |
| --- | --- | --- |
|  | Inch | mm |
| Valve stem orifice | 0.025 | 0.64 |
| Valve body housing orifice | 0.035 | 0.89 |
| Bubbler orifice | 0.030 | 0.76 |
| Dip tube | 0.15 | 3.8 |
| Actuator orifice | 0.025 | 0.64 |

A two-second application from the container expelled 0.8 g of antiperspirant composition, and delivered 0.060 g of aluminum chlorhydroxide to the skin. The composition was effective for one day to inhibit perspiration.

EXAMPLE 7

An aerosol antiperspirant composition was prepared having the following formulation:

|  | Parts By Weight |
| --- | --- |
| Aluminum chlorhydroxide | 10.0 |
| Palmitic acid (solid, titer 56° C.) | 0.1 |
| Isopropyl myristate | 10.0 |
| Silicone gum, 10-20 million centistokes | 0.4 |
| Silicone fluid, 500 centistokes | 1.5 |
| Cab-O-Sil silica | 1.0 |
| Propane | 10.0 |
| Isobutane | 67.0 |

The colloidal silica was combined with the isopropyl myristate and palmitic acid, and mixed in a Waring Blendor at high speed for 5 minutes. The silicone gum was dissolved in the silicone fluid by heating with stirring. The dispersion was then combined with the silicone solution and aluminum chlorhydroxide, and homogenized. The composition was filled into an aerosol container of the type shown in FIGS. 1 and 2 of U.S. Pat. No. 4,019,657 patented Apr. 26, 1977, having the following dimensions:

|  | Internal Diameter | |
| --- | --- | --- |
|  | Inch | mm |
| Valve stem orifice | 0.025 | 0.64 |
| Foam chamber, height × diameter | 1.0 × 0.3 | 25 × 8 |
| Bubbler orifice | 0.040 | 1.0 |
| Capillary dip tube | 0.040 | 1.0 |
| Actuator orifice | 0.025 | 0.64 |

The contents of the container was then pressurized with the isobutane and propane.

A two-second application expelled 1.0 g of the composition, and delivered to the skin 0.060 g aluminum chlorhydroxide. This was effective to inhibit perspiration for one day.

EXAMPLE 8

An aerosol antiperspirant composition was prepared having the following formulation:

|  | Parts by Weight |
| --- | --- |
| Aluminum chlorhydroxide | 10.0 |
| Behenic acid (solid, titer 65° C.) | 0.2 |
| Cab-O-Sil silica | 0.5 |
| Isopropyl myristate | 9.3 |
| 1,1-Difluoroethane | 70.0 |
| 1,1,2-Trichlorotrifluoroethane | 10.0 |

The colloidal silica was combined with the behenic acid and isopropyl myristate and mixed in a Waring Blendor at high speed for five minutes. The composition was filled into an aerosol container of the type shown in FIGS. 1 and 2 of U.S. Pat. No. 4,019,657 patented Apr. 26, 1977, having the dimensions shown below, and then pressurized with a mixture of 1,1-difluoroethane and 1,1,2-trichlorotrifluoroethane.

|  | Internal Diameter | |
| --- | --- | --- |
|  | Inch | mm |
| Valve stem orifice | 0.020 | 0.51 |
| Foam chamber, height × diameter | 1.0 × 0.3 | 25 × 8 |
| Bubbler orifice | 0.040 | 1.0 |
| Capillary dip tube | 0.040 | 1.0 |
| Actuator orifice | 0.025 | 0.64 |

A two second application from the container expelled 1.0 g of antiperspirant composition, and deposited 0.065 g of aluminum chlorhydroxide on the skin. The composition was effective for one day in inhibiting perspiration.

EXAMPLE 9

An aerosol antiperspirant composition was prepared having the following formulation:

|  | Parts By Weight |
| --- | --- |
| Aluminum chlorhydroxide | 12.0 |
| Arachidic acid (titer 65° C.) | 0.2 |
| Butyl stearate | 7.3 |
| Cab-O-Sil silica | 0.5 |
| Cyclopropane | 56.0 |
| Trichlorofluoromethane | 24.0 |

The colloidal silica was combined with the arachidic acid and butyl stearate and mixed in a Waring Blendor at high speed for 5 minutes. The composition was then filled into aerosol containers of the type shown in FIGS. 1, 1A and 2 of Ser. No. 706,857 filed July 19, 1976. The composition was then pressurized by the addition of a mixture of trichlorofluoromethane and cyclopropane.

The aerosol container had the following dimensions:

|  | Internal Diameter | |
|---|---|---|
|  | Inch | mm |
| Valve stem orifice | 0.020 | 0.51 |
| Bubbler orifice | 0.035 | 0.89 |
| Capillary dip tube | 0.040 | 1.0 |
| Actuator orifice | 0.020 | 0.51 |

A two-second application from the container expelled 1.1 g of antiperspirant composition, and deposited 0.080 g of aluminum chlorhydroxide on the skin. The composition was effective for one day in inhibiting perspiration.

EXAMPLE 10

A trial-and-error test can be applied to ascertain the amount of carboxylic acid that should be employed in any particular composition, by actually noting the adhesiveness of the spray deposit to the skin. The test simulates the rubbing action due to the normal movement of the arms, in the presence of a small amount of moisture. A two-second spray at a distance of six inches is applied to the back of one hand or to the forearm. After allowing a few minutes for the propellant to evaporate, a single drop of water is placed on the deposit, and rubbed firmly with the index finger of the other hand. This is repeated with a second and a third drop of water. If the antiperspirant deposit rolls and flakes, and can be brushed off the skin, the amount of solid carboxylic acid should be increased until good adherence is obtained.

When a liquid carboxylic acid is used in comparable amount, adhesion is very poor. A very much larger amount is needed to obtain good adhesion, but then the deposit adheres so tenaciously that it is virtually impossible to remove with soap and water.

This effect can be observed by spraying the antiperspirant onto either a hairy underarm, or the hairy portion of the forearm. After allowing a few minutes for the propellant to evaporate, the sprayed area is washed with bar soap and water. The hair becomes entangled and matted, and extreme difficulty is experienced in removing the deposit.

This was demonstrated by a test series employing six subjects using the following compositions:

|  | Parts by Weight | |
|---|---|---|
|  | Control | Example 10 |
| Aluminum chlorhydroxide | 9.0 | 9.0 |
| Isostearic acid (titer 9° C.) | 1.3 | — |
| Stearic acid, triple pressed (titer 55° C.) | — | 0.23 |
| Cab-O-Sil | 0.9 | 0.9 |
| Isopropyl myristate | 8.8 | 9.9 |
| Isobutane | 64.0 | 64.0 |
| Propane | 16.0 | 16.0 |

The subjects all found great difficulty removing deposits containing isostearic acid. One subject gave up after repeated washing, and used a scissors to remove the matted hair. However, deposits containing stearic acid were readily removed.

A series of six formulations A to F based on the above composition were prepared using the carboxylic acids listed in the Table below to determine the minimum amount of carboxylic acid required for good adhesion. The total quantity of carboxylic acid and isopropyl myristate was held at 10.1 parts by weight, and as the amount of carboxylic acid was increased, the amount of isopropyl myristate was reduced. In each case, the proportion of carboxylic acid was increased in stages until good adhesion was obtained. This minimum is given in the Table.

|  | Parts by Weight | | | | | |
|---|---|---|---|---|---|---|
|  | A | B | C | D | E | F |
| Aluminum chlorhydroxide | 9.0 | 9.0 | 9.0 | 9.0 | 9.0 | 9.0 |
| Stearic acid triple pressed (Titer 55° C.) | 0.28 | — | — | — | — | — |
| Stearic acid (Titer 65° C.) | — | 0.18 | — | — | — | — |
| Palmitic acid (Titer 56° C.) | — | — | 0.32 | — | — | — |
| Myristic acid (Titer 53° C.) | — | — | — | 0.41 | — | — |
| Isotearic acid (Titer 9° C.) | — | — | — | — | 1.35 | — |
| Oleic acid (Titer 5° C.) | — | — | — | — | — | 1.35 |
| Isopropyl myristate | 9.9 | 9.9 | 9.8 | 9.7 | 8.8 | 8.8 |
| Cab-O-Sil | 0.9 | 0.9 | 0.9 | 0.9 | 0.9 | 0.9 |
| Isobutane | 64.0 | 64.0 | 64.0 | 64.0 | 64.0 | 64.0 |
| Propane | 16.0 | 16.0 | 16.0 | 16.0 | 16.0 | 16.0 |

It is apparent that very much larger amounts of liquid fatty acid are needed.

Having regard to the foregoing disclosure, the following is claimed as the inventive and patentable embodiments thereof:

1. An aerosol antiperspirant composition that is highly concentrated with respect to the active antiperspirant, and capable of being dispensed from aerosol containers of the foam type at a low delivery rate in a propellant gas:liquid ratio within the range from about 10:1 to about 40:1 comprising, in combination, a liquid phase comprising a nonvolatile miscible organic liquid in an amount within the range from about 0.1 to about 30% by weight of the composition; an antiperspirant salt in an amount within the range from about 8 to about 30% by weight of the composition; a bulking agent in an amount within the range from about 0.1 to about 5% by weight of the composition; a liquefied propellant having a vapor pressure of at least 2.4 atmospheres absolute at 21° C., in an amount of at least 0.15 mole per atmosphere absolute pressure at 21° C. per 100 g of composition to generate an expelled gas:liquid ratio within the range from about 10:1 to about 40:1 and a solid saturated aliphatic carboxylic acid having from about fourteen to about twenty-two carbon atoms in a straight chain and in an amount within the range from about 0.1 to about 5% by weight of the composition to improve adherence of the antiperspirant salt to the skin.

2. An antiperspirant composition according to claim 1, in which the antiperspirant salt is an aluminum salt.

3. An antiperspirant composition according to claim 2, in which the antiperspirant salt is aluminum chlorhydroxide.

4. An antiperspirant composition according to claim 2, in which the antiperspirant salt is aluminum chloride.

5. An antiperspirant composition according to claim 1, in which the antiperspirant salt is a zirconium salt.

6. An antiperspirant composition according to claim 5, in which the antiperspirant salt is a mixture of aluminum chlorhydroxide and zirconium chlorhydroxide.

7. An antiperspirant composition according to claim 1, in which the nonvolatile liquid is a carboxylic acid ester of an alcohol, the ester having from about twelve to about twenty-six carbon atoms.

8. An antiperspirant composition according to claim 7, in which the ester is isopropyl myristate.

9. An antiperspirant composition according to claim 1, in which the bulking agent comprises colloidal silica having a particle size below 10 microns in diameter.

10. An antiperspirant composition according to claim 1, in which the bulking agent comprises a hydrophobic clay having a particle size below 10 microns in diameter.

11. An antiperspirant composition according to claim 1, in which the propellant is a hydrocarbon propellant.

12. An antiperspirant composition according to claim 1, in which the propellant is a halocarbon propellant.

13. An antiperspirant composition according to claim 1, in which the propellant is isobutane.

14. An antiperspirant composition according to claim 13, comprising a mixture of isobutane and another hydrocarbon or halocarbon propellant according to claim 1.

15. An antiperspirant composition according to claim 1, in which the carboxylic acid is an aliphatic acid selected from the group consisting of palmitic and stearic acid.

16. An aerosol antiperspirant composition that is highly concentrated with respect to the active antiperspirant, comprising, in combination, a liquid phase comprising a nonvolatile miscible organic liquid in an amount within the range from about 0.1 to about 30% by weight of the composition; an antiperspirant salt in an amount within the range from about 8 to about 30% by weight of the composition; a bulking agent in an amount within the range from about 0.1 to about 5% by weight of the composition; a liquefied propellant having a vapor pressure of at least 2.4 atmospheres absolute at 21° C.; and a solid saturated aliphatic carboxylic acid having from about fourteen to about twenty-two carbon atoms in a straight chain and in an amount within the range from about 0.1 to about 5% by weight of the composition to improve adherence of the antiperspirant salt to the skin.

17. An antiperspirant composition according to claim 16, in which the antiperspirant salt is an aluminum salt.

18. An antiperspirant composition according to claim 17, in which the antiperspirant salt is aluminum chlorhydroxide.

19. An antiperspirant composition according to claim 17, in which the antiperspirant salt is aluminum chloride.

20. An antiperspirant composition according to claim 16, in which the antiperspirant salt is a zirconium salt.

21. An antiperspirant composition according to claim 16, in which the antiperspirant salt is a mixture of aluminum chlorhydroxide and zirconium chlorhydroxide.

22. An antiperspirant composition according to claim 16, in which the nonvolatile liquid is a carboxylic acid ester of an alcohol, the ester having from about twelve to about twenty-six carbon atoms.

23. An antiperspirant composition according to claim 22, in which the ester is isopropyl myristate.

24. An antiperspirant composition according to claim 16, in which the bulking agent comprises colloidal silica having a particle size below 10 microns in diameter.

25. An antiperspirant composition according to claim 16, in which the bulking agent comprises a hydrophobic clay having a particle size below 10 microns in diameter.

26. An antiperspirant composition according to claim 16, in which the propellant is a hydrocarbon propellant.

27. An antiperspirant composition according to claim 16, in which the propellant is a halocarbon propellant.

28. An antiperspirant composition according to claim 16, in which the propellant is isobutane.

29. An antiperspirant composition according to claim 28, comprising a mixture of isobutane and another hydrocarbon or halocarbon propellant according to claim 1.

30. An antiperspirant composition according to claim 16, in which the carboxylic acid is an aliphatic acid selected from the group consisting of palmitic and stearic acid.

* * * * *